United States Patent [19]

Smith et al.

[11] Patent Number: 5,069,221
[45] Date of Patent: Dec. 3, 1991

[54] DISPLACEMENT SENSOR AND MEDICAL APPARATUS

[75] Inventors: Edmund S. Smith; John Davies, both of North Wales, United Kingdom

[73] Assignee: Densa Limited, North Wales, United Kingdom

[21] Appl. No.: 540,314

[22] Filed: Jun. 18, 1990

Related U.S. Application Data

[63] Continuation of Ser. No. 139,648, Dec. 30, 1987, abandoned.

[51] Int. Cl.$^5$ .............................................. A61B 5/08
[52] U.S. Cl. ................................... 128/721; 324/226; 324/207.2
[58] Field of Search ........................ 128/721, 722, 716; 324/207.20, 207.14; 73/DIG. 3

[56] References Cited

U.S. PATENT DOCUMENTS

| | | | |
|---|---|---|---|
| 3,547,106 | 12/1970 | Barnman | 128/721 |
| 3,558,052 | 4/1972 | Alter | 128/721 |
| 3,911,899 | 10/1975 | Hattes | 128/721 |
| 4,487,074 | 12/1984 | Herden | 73/DIG. 3 |
| 4,517,514 | 5/1985 | Howell | 324/207 |
| 4,576,179 | 3/1986 | Manus et al. | 128/721 |
| 4,627,292 | 12/1986 | DeKrone | 324/207 |
| 4,691,185 | 9/1987 | Leubier et al. | 324/207 |

FOREIGN PATENT DOCUMENTS 0093546  11/1983  European Pat. Off. ............ 122/721

Primary Examiner—William E. Kamm
Assistant Examiner—Robert L. Nasser, Jr.
Attorney, Agent, or Firm—Grant L. Hubbard

[57] ABSTRACT

A displacement sensor which is battery operated and suitable for use as a respiratory monitor to detect the onset of apnoea in infants or post operative patients is disclosed. The sensing device is easily attached to the patient by an elasticated belt, together with associated monitoring electronics in which the sensor signal is compared with a floating reference level in a level detector which is connected through a NAND gate 3 to prevent a timer 4 timing out while respiration signals are present. Cessation of respiratory movement for greater than 10 or 20 seconds is indicated by both audible and visual alarms 14 and 15. In another embodiment the sensor can be used to detect eye movements in a patient. Medical monitoring apparatus is also provided, said apparatus including a heart rate monitoring means and/or respiration monitoring means.

9 Claims, 7 Drawing Sheets

PATIENT WITH ELECTRODES

DISPLACEMENT SENSOR AND MEDICAL APPARATUS

This is a continuation of application Ser. No. 139,648 filed on Dec. 30, 1987, now abandoned.

FIELD OF THE INVENTION

This invention relates to a displacement sensor and to medical apparatus, such as relative movement sensors generally, respiratory monitors, eye movement sensors, heart beat and heart rate sensors, and the like, for example.

BACKGROUND OF THE INVENTION

Displacement sensors which come in many different forms are usually designed to give a quantitative measurement of the displacement being measured. Often, however, a quantitative output is not required, and an indication that movement has occurred suffices.

One particular type of displacement sensor with which this invention is concerned is respiratory monitors. A respiratory monitor is already known which has a sensor for detecting mechanically the breathing of a patient and an electronic control unit which provides output signals determined by the state of the sensor. The sensor in the known monitor comprises a flattened, hollow, rubber or plastic bulb containing an air bubble and connected by tubing to an air-pressure transducer. The sensor is strapped around a patient's chest or abdomen whereby expansion of the lungs causes the bulb to be squashed and the air pressure therewithin to be increased. The pressure increase results in an electrical signal from the transducer which is detected by the electronic control unit to provide an indication of the incidence of respiration by the patient.

A problem in practice with this known system is that it reacts only to increases in pressure at the transducer. Thus, for example, if the patient should roll over and lie on top of the sensor it could be deformed permanently so that no further increase in pressure can result even if the patient is, in fact, breathing normally. Thus, the known system is liable to false alarms due primarily to the type of sensor used but also to the fact that the electronic control unit only reacts to an increase in pressure in the sensor.

SUMMARY OF THE INVENTION

It is an object of the present invention to provide an improved displacement sensor. In one particular form, it is an object of the present invention to provide a respiratory monitor in which the disadvantages of the known system are substantially avoided.

According to one aspect of the present invention, a displacement sensor is provided which is characterized in that a qualitative indication of relative movement between the sensor and the surface to which it is attached is given.

According to a second aspect of the present invention, there is provided a displacement sensor characterized in that it comprises (a) a housing formed of a resilient material and incorporating a first chamber and spaced therefrom a second chamber; (b) a displacement transducer mounted within one of said two chambers within said housing; (c) an activator for said displacement transducer mounted within the other of said two chambers within said housing; and (d) an output arrangement for delivering a signal from the displacement transducer when the sensor is actuated.

Preferably the displacement transducer is a Hall effect device (most preferably mounted on a circuit board or on a chip) and the activator therefor is a permanent magnet. The activating magnet will generally be a small magnet, preferably with dimensions in the millimeter range, and having a high magnetic flux density. Typically, we have found it advantageous to use a cylindrical magnet 1.5 mm high by 3.0 mm diameter formed of sintered samarium-cobalt. A suitable material is that known as "Supermagloy S2" manufactured by Swift Levick Supermagloy Limited of Swindon, England. Where the output from the sensor is an electrical output, the output arrangement can take the form of one or more electrical leads or cables.

The housing is advantageously formed from a synthetic polymeric material, silicone rubber being presently preferred.

The housing preferably includes an upper relatively thick walled part, within the wall of which said first chamber is disposed, and a lower relatively narrow walled portion which defines the second chamber. With this arrangement, a permanent magnet may be disposed within the first chamber and a Hall effect device may be disposed within the second chamber. The first chamber preferably debouches into a cavity which constitutes the second chamber, the Hall effect device being spaced from the entry to said first chamber. The upper, thick walled part of the housing may incorporate one or more lugs or other projections which extend downwardly towards or into the second chamber, such projection(s) serving to maintain a predetermined minimum spacing between the magnet in the first chamber and the Hall effect device in the second chamber.

The presently preferred embodiment of the sensor comprises essentially a silicone rubber cap in which a magnet is mounted, housing a displacement transducer (a Hall effect device) mounted on a small circular printed circuit board. Movement produces a change in the magnetic field surrounding the device which produces a change in its electrical output.

According to a further aspect of the present invention, there is provided a displacement sensor characterized in that it comprises (a) a housing formed of a resilient material and including a relatively thick walled cap portion incorporating a first chamber; (b) depending from said cap portion, a downwardly and outwardly extending frustoconical wall portion; (c) connected to said frustoconical wall portion, a relatively thin walled portion defining a second chamber; (d) a Hall effect device mounted within said second chamber; (e) a permanent magnet mounted within said first chamber; and (f) an electrical arrangement in electrical contact with said Hall effect device and arranged to deliver an output signal when the sensor is subjected to movement such as to alter the relative position between said Hall device and said permanent magnet.

In accordance with another aspect of the present invention, there is provided a respiratory monitor comprising a sensing device having a permanent magnet mounted resiliently relative to a Hall effect sensor, the sensing device being adapted to respond to respiratory action in a patient to whom the sensing device is attached to provide changes in the level of the output voltage from the sensor and a monitoring circuit which monitors electronically the output of the Hall effect sensor and responds to change in sensor output to indicate that respiration has occurred.

Preferably, the monitoring circuit includes a timer which is arranged to be reset upon the detection of a change in voltage level from the sensor indicative of respiratory action; if the timer is not so reset within a preselectable time period, then an alarm is caused to be raised.

Advantageously, the alarm is both visual and audible. If, on having raised the alarm, the monitoring circuit then detects a breathing action, the audible alarm may be cancelled but the visual alarm continued for a predetermined period. If respiratory action does not recommence, both audible and visual alarms preferably continue until reset by an investigating person.

Preferably, the monitoring circuit includes a level detector which is adapted to detect changes in the prevailing output level of the sensor, irrespective of what the prevailing output level might be. For this purpose, the level detector comprises a comparator, the reference level of which is provided by a square wave signal supplied by an oscillator.

Preferably, the level detector includes two series connected comparators, the first comparator receiving at its one input the voltage output of the sensor and at its other (a) the integrated output of the sensor and (b) said square wave signal, the output of the first comparator being coupled to the input of the second comparator by way of a diode pumping circuit and a parallel capacitor, the other input of the second comparator being provided with a fixed reference level, whereby when the sensor output remains constant an oscillating output is obtained from the first comparator which charges said parallel capacitor and holds the second comparator in one switching state, but when a change in sensor output occurs a steady signal is temporarily obtained from the first comparator which caused the voltage on the parallel capacitor to decay and the second comparator to change switching states, thereby indicating that respiration has occurred.

In a further development of the invention, the displacement transducer is arranged to detect non-respiratory movements, for example eye motion. In this embodiment, the housing incorporates a single chamber which contains the displacement transducer (e.g. a Hall effect device), and the activator (e.g. a permanent magnet) is secured to a part of a patient where movement is to be detected, e.g. to the eyelid of a patient. The housing containing the Hall effect device is then positioned close to the activator so that any movement of the part to which the magnet is secured will result in a signal from the transducer. Accordingly, in another aspect, the present invention provides a displacement sensor characterized in that it comprises (a) a housing formed of a resilient material incorporating a chamber; (b) a displacement transducer mounted within said chamber; and (c) an output arrangement for delivering a signal from the displacement transducer when the sensor is actuated. Generally, the displacement transducer will be a Hall effect device. Also, the sensor is preferably constructed so that it can be located over part of a patient (e.g. over an eye) where movement is to be detected.

Accurate information about eye movements in patients has, in the past, been very difficult to obtain. By means of this embodiment of the present invention, we have found that accurate data on eye movement can be obtained with relatively little discomfort for the patient.

It will be appreciated that the housing containing the Hall effect device must be placed to the magnet which in turn is secured to, for example, a patient's eyelid. To achieve this arrangement, the housing can be supported on an adjustable frame which is movable towards and away from a patient's body.

In one preferred embodiment, the displacement sensor is arranged to count and to display the breathing rate of a patient. The breathing rate is advantageously determined over a 30-second averaging period (because of the relatively low rates involved it should be meaningless to determine a breathing rate based on a 5-second averaging period say). A display of breaths/minute is preferably provided which is updated every 30 seconds.

An alarm is raised if the breathing rate drops below a pre-settable value (say 10 breaths/minute) or if it rises above a pre-settable value (say 24 breaths/minute for an adult or 60 for an infant).

On raising an alarm the display is preferably latched so that the offending rate is held on the display until reset by the operator.

In a further advantageous development, the present invention provides medical apparatus which consists of, or incorporates, a heart beat detection system based on a transthoracic impedance technique. More particularly, in a further aspect, the invention provides medical monitoring apparatus comprising means for detecting and displaying data relating to a patient's heart rate, optionally together with further means for detecting and displaying data relating to the patient's respiration, wherein said heart rate monitoring means comprises: (a) a plurality of inputs for electrodes which, in use, are positioned on the patient's abdomen; (b) an operational amplifier for amplifying the signal fed to said inputs by the electrodes; (c) a full wave rectification circuit arranged to cut upon the output of the operational amplifier so as to reduce the effect of unwanted signal pick up from the electricity supply frequency and to deliver a DC signal whose magnitude is dependent on the unwanted signal element and on which there is superimposed the wanted signal indicative of the patient's heart rate; and (d) counting and display circuits and display means arranged to display parameters associated with the heart rate of the patient. Details of the operation of this heart rate monitor will be given hereinafter with reference to the accompanying drawings.

The invention is described further hereinafter, by way of example only, with reference to the accompanying drawings, wherein:

DESCRIPTION OF THE PREFERRED EMBODIMENTS

Figure 1:
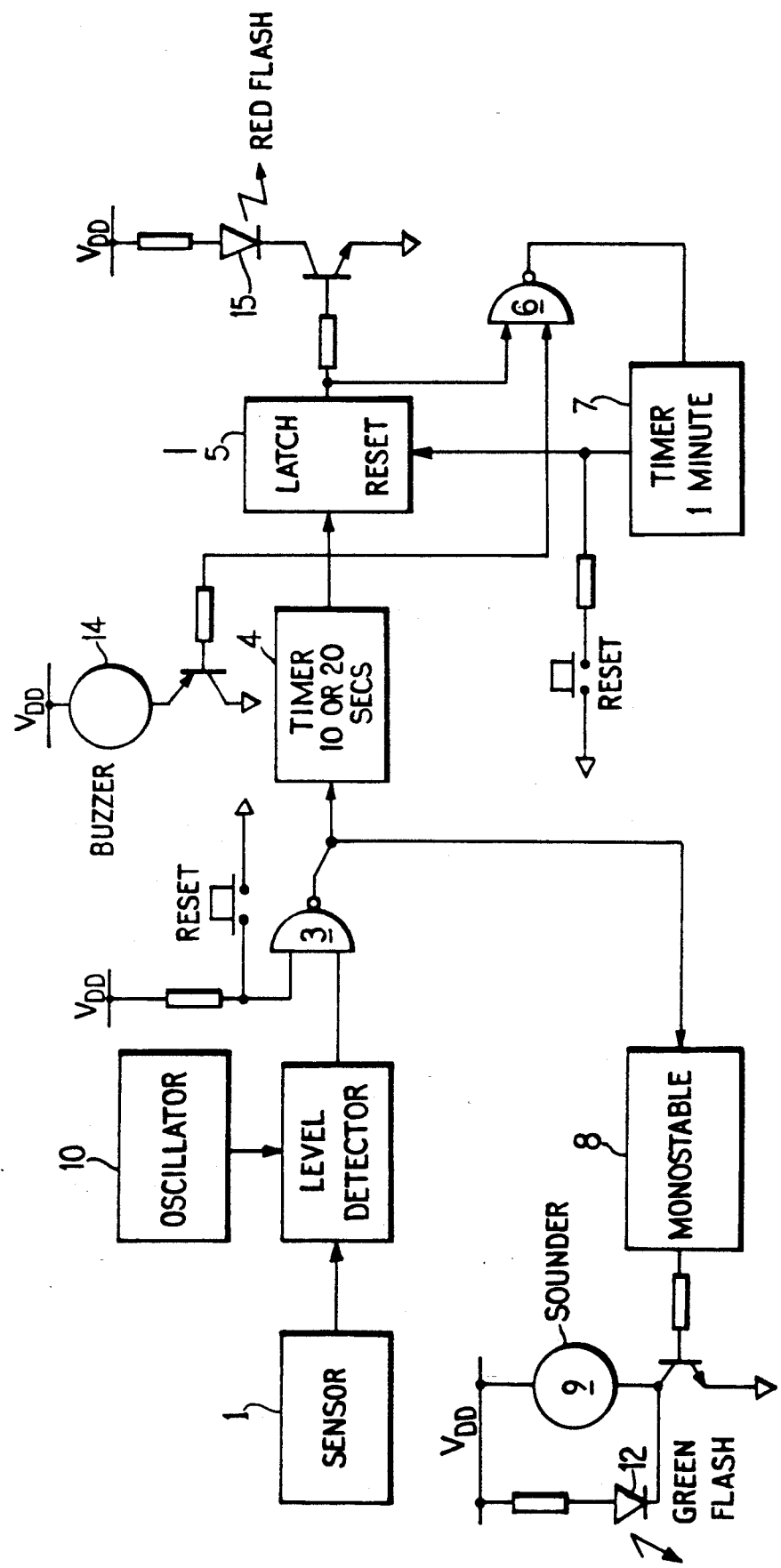
FIG. 1 is a block circuit diagram showing one embodiment of a respiratory monitor in accordance with the present invention.

With reference first to FIG. 1, the monitor uses a sensor 1 which is attached to a patient's body to generate electrical signals responsive to respiration of the patient. The sensor (shown in detail in FIGS. 4 and 5) includes a permanent magnet which is disposed in a flexible mounting in close proximity (for example 1 mm) to a Hall effect sensing device. The magnet can, for example, be suspended over the Hall effect sensing device by means of a rubber or plastics diaphragm or simply by means of a layer of a resilient rubber foam material. The sensor is strapped by a belt or harness or otherwise mounted on the patient (preferably on the patient's abdomen) such that upon respiration the relative positions of the magnet and Hall effect device change, whereby to generate an output signal from the sensor.

Normally, with the patient lying on his back and the sensor strapped to his abdomen, respiratory action causes the rubber foam to compress and the magnet to move towards the sensor thereby generating an output voltage of specific polarity. However, it will be noted that, depending upon the position of the patient, the actual signal level and signal polarity which is generated during respiration cannot be predicted. For example, the patient may be lying on the sensor so that the rubber is already partially compressed. For this reason, as described hereinafter, the detection circuitry is adapted to respond to any signal change from the sensor above a certain threshold level corresponding to the sensitivity of the circuitry. The detection circuitry is therefore not looking for any particular voltage level but for a change in the prevailing level, whatever the latter level might be.

The sensor 1 which is attached to the patient's body thus detects respiratory movement in the patient and transmits an electrical signal to the monitoring electronics. The latter part of the system can be located at a position remote from the sensor 1.

Figure 2:
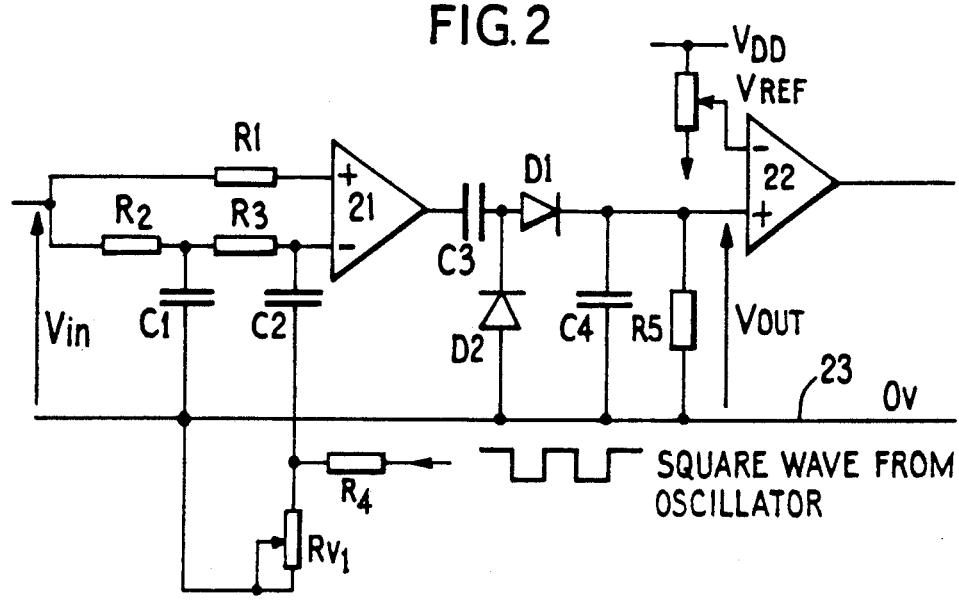
FIG. 2 shows a detail of the circuit diagram of FIG. 1.

The sensor signal is applied to a level detector 2 which, as described further hereinafter with reference to FIGS. 2 and 3, is provided with a floating reference level by means of an oscillator 10. The output of the level detector forms one input of a NAND gate 3 whose other input is connected to a fixed supply voltage $V_{DD}$. The output NAND gate 3 is connected to the control input of an electronic timer 4 and also the trigger input of a monostable 8.

The output of the NAND gate 3 is normally low, and this is arranged to cause the timer 4 to time out. As explained further hereinafter, each time a respiratory action is sensed by the level detector 2, the output of the NAND gate 3 is caused to go high so resetting the timer and initiating another timing period. Each time the output of NAND gate 3 goes high, the monostable 8 is triggered. This is arranged to produce an audible "click" from an electronic sounder 9, together with a flash of green light from a green LED 12. The purpose of the click and flash is to indicate to a person monitoring the alarm that respiratory action is taking place and that the electronics is functioning.

The timer 4 times out in either ten or twenty seconds selectable by a front panel switch (not shown). If respiratory action fails and the timer does in fact time out, then the alarm is raised by the timer energizing a buzzer 14. At the same time a latch 5 is set which causes a red LED 15 to flash. If then respiratory action should recommence, the audible alarm 14 is stopped as a result of the timer being reset. At the same time, the output of a further NAND gate 6 is arranged to go low to cause a further timer 7 to time out. On timing out, for example after one minute, the output of the timer 7 resets the latch 5 so turning off the red flashing indicator 15. Thus, even though respiration recommences, the red indicator 15 flashes for a period of one minute to indicate to the person monitoring the alarm that a break in normal respiration has occurred.

The structure and operation of the level detector 2 are now described in more detail with reference to FIGS. 2 and 3.

The sensor signal $V_{in}$ is applied to the non-inverting input (+) of an operational amplifier comparator 21 by way of a resistor $R_1$ and to the inverting input (−0) by way of the series combination of two resistors $R_2$ and $R_3$. The junction of the resistors $R_2$ and $R_3$ is coupled to the $O_V$ line 23 by way of a capacitor $C_1$.

The inverting input of comparator 21 is also connected to the $O_v$ line by way of the series combination of a capacitor $C_2$ and a variable resistor $R_v1$. A square wave derived from the oscillator 10 is injected at the junction of the capacitor $C_2$ and variable resistor $R_{v1}$ by way of a resistor $R_4$.

The output of the comparator 21 is led to the non-inverting input of a second operational amplifier comparator 22 by way of the series combination of a capacitor $C_3$ and a diode $D_1$. The junction of the capacitor $C_3$ and the diode $D_1$ is coupled to the $O_v$ line by way of a diode $D_2$. The non-inverting input of the comparator 22 is connected to the $O_v$ line by way of the parallel combination of a capacitor $C_4$ and a resistor $R_5$. The inverting input of a comparator 22 is provided with a d.c. reference level $V_{re}$ by means of a variable resistor $RV_2$ connected across the supply voltage. The output of the comparator 22 provides the output of the level detector coupled to the NAND gate 3, in accordance with FIG. 1.

In operation, in order to prevent the timer 4 from timing out, the output of comparator 22 must be arranged to go low each time a breath occurs. For the output of comparator 2 to go low, the voltage $V_{out}$ at its non-inverting input must drop below $V_{ref}$. This is achieved as follows:

The input voltage $V_{in}$ can be at any value (within the linear range of the sensor output) depending on the degree of compression of the sensing diaphragm. However, a respiratory action will always result in at least a small change in $V_{in}$.

It will be appreciated that a conventional comparator arrangement cannot be used to detect such changes since an arrangement would normally use a fixed reference against which the input voltage $V_{in}$ would have to be compared. To overcome this problem, the present circuit provides a reference which floats with the prevailing level of $V_{in}$, the magnitude of the reference being set by $RV_1$.

Figure 3A:
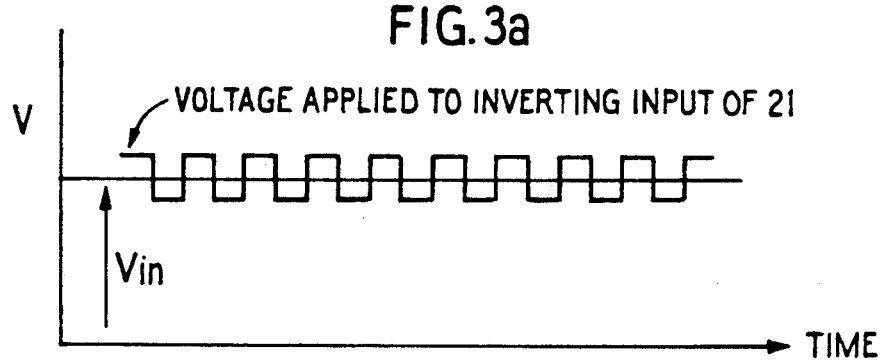
FIGS. 3a and 3b are diagrammatic graphs for use in explaining the operation of the portion of the circuit shown in FIG. 2.

The floating reference is achieved by use of the square wave applied across the potential divider formed by $R_4$ and $RV_1$. The capacitor $C_2$ decouples the voltage across $RV_1$ and impresses it upon the voltage appearing at the inverting input of the comparator 21. If $V_{in}$ is constant (i.e. no respiratory action is occurring), the voltage applied to the inverting and non-inverting inputs of comparator 21 would be the same (ignoring for the moment the impressed voltage coupled by $C_2$). Under these conditions, when the impressed voltage is taken into account, the output of comparator 21 switches at the oscillator frequency as the voltage at the inverting terminal swings above and below the voltage at the non-inverting terminal. This situation is illustrated in FIG. 3a.

The components $C_3$, $D_1$, $D_2$, act as a so-called diode pump circuit serving to charge capacitor $C_4$. It will be appreciated that, providing the output of comparator 21 continues to oscillate, the voltage $V_{out}$ across the capacitor $C_4$ will be maintained. However, if the output of comparator stops oscillating and is either permanently high or low, then the voltage $V_{out}$ across $C_4$ will disappear (reduce to zero).

Figure 3B:
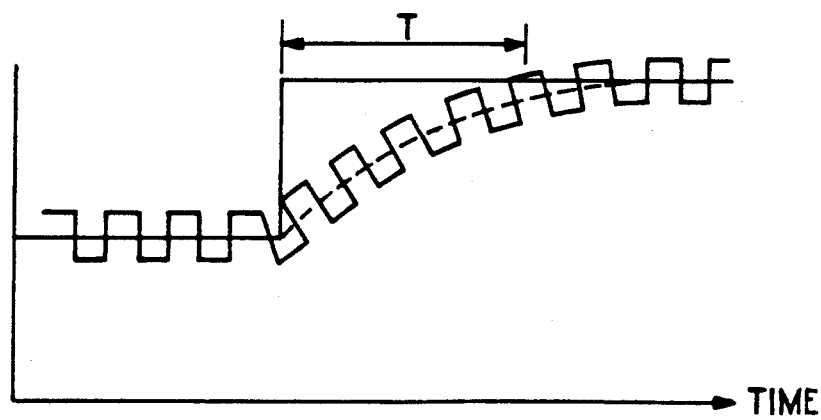

Now $V_{in}$ changes each time respiratory action takes place. The voltage at the non-inverting terminal of comparator 21 follows $V_{in}$ instantly, whereas the voltage at the inverting terminal does not, due to capacitor $C_1$ charging or discharging. The effect is illustrated in FIG. 3b for an imagined step change in $V_{in}$. Referring to FIG. 3b, over the period T, the voltage at the non-inverting terminal always exceeds that at the inverting terminal, so that the output of comparator 21 is permanently high for this period. Since no pumping voltage is applied to the circuit $C_3$, $D_1$, $D_2$, the voltage $V_{out}$ decays to zero. As soon as $V_{out}$ falls below $V_{ref}$ the output of comparator 22 is caused to switch to its low value, signifying that respiratory action has taken place.

It was assumed above that the change in $V_{in}$ was a step rise. It will be appreciated that a step fall in $V_{in}$ would cause the output of comparator 21 to go low, but again $V_{out}$ would decay to zero, signifying respiratory action.

The sensitivity of the comparator 21 is set by the voltage appearing across $RV_1$. In practice this can be set to a relatively low level e.g. 10 mv peak.

Thus, whatever the direction and magnitude of the change in $V_{in}$ (above a threshold magnitude), the circuit will detect such changes as being the result of respiratory action and will react accordingly to prevent timer 4 from timing out.

The monitoring electronics can be housed in any suitable manner. One convenient arrangement is for the monitoring electronics to be housed in a small handheld plastic box. The timing out time (ten or twenty seconds—or any other desired period) is selected by a panel switch on the box. Such a monitor may be powered by batteries, for example four 1.5-volt dry batteries disposed in the box, and is therefore inherently safe. A low voltage indicator can be incorporated to warn when batteries need changing.

Figure 4:
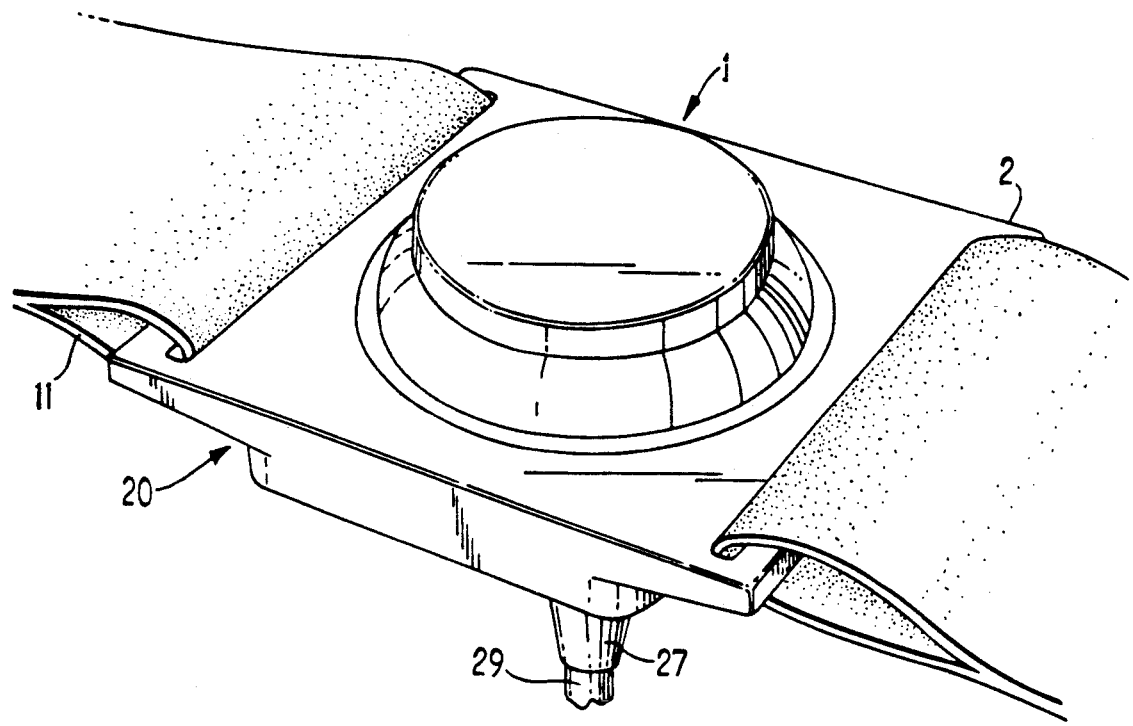
FIG. 4 shows in perspective a sensor having an electrical cord for connection to an electronic monitoring arrangement.

With reference to FIG. 4 of the drawings, the displacement sensor (which is suitable for use inter alia as a respiration monitor) comprises a housing 1 which has lateral extensions such as 2 for receiving a belt or similar fastening device 11. An electrically insulating sheathing 27 surrounds an output cable 29.

Figure 5:
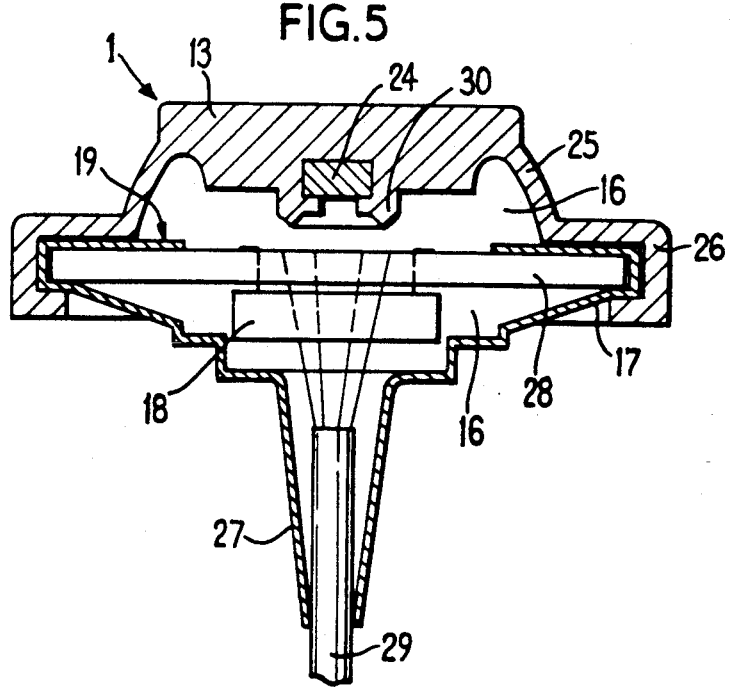
FIG. 5 is a schematic cross-section through the sensor of FIG. 4 indicating the method of mounting the Hall device and its associated magnet.

Referring now to FIG. 5, the housing 1 comprises an upper, relatively thick walled cap portion 13 which includes a recess in which is mounted a permanent magnet 24. An annular ring 30 projects downwardly from the inside of cap 13 in the region just below magnet 24. Ring 30 has a "V"-shaped profile as shown. Downwardly and outwardly extending frustoconical wall portions 25 join cap portion 13 to a relatively thin-walled portion 26 which together with the inward facing surface of cap portion 13 define an internal cavity or chamber 16. Within this chamber 16 there is located a printed circuit board 28 onto which a Hall effect device 18 is soldered.

Electrical connection to the sensor is effected by a four-cored cable 29, soldered to the printed circuit board 28.

The sheathing 27 is in the form of a thin-walled rubber shroud which fits tightly over the printed circuit board 28 and cable 29 and is sculptured to fit snugly over the Hall effect device 18 and to ensure that the sensor assembly sits securely in the plastics retaining plate 20.

The housing is formed of a resilient silicone rubber material and is arranged so that it clips over an extension 17 of sheathing 27 which in turn is folded over as at 19 to hold the printed circuit board 28. The whole assembly is then held by the plastic retaining plate 20 through which the retaining strap 11 is threaded, as shown in FIG. 4.

In usage the flat head of the cap 13 is held in contact against the surface to be monitored for movement. Movement causes deflection of the cap containing magnet 24 relative to the Hall effect device 18, thereby producing a change in the magnetic field coupling with the Hall device 18, and hence a change in its output.

The walls of the silicone rubber housing 1, and in particular the cap 13 and wall portions 25, have a specially designed geometry as shown in FIG. 5 and this leads to a particular characteristic such that the head of the cap 13 is compliant with the movement of the surface being monitored. This enables minute movements to be detected. The ability of the cap 13 to follow such movements is enhanced by the geometry of wall portion 26 and of sheathing 27 and 17 which, together with the structure of molded plastic retaining plate 20, enables the cap 13 to retract into the cavity 16, but not so far that its ability to track surface movement is impaired. This feature is enhanced for surfaces which come within the boundary of the retaining plate 20 by the resilient rubber ring 30 integral with the silicone cap 13 and having a profile in the form of a "V" ring; this assists in preventing the magnet 24 from being held fixed into the surface on which it would otherwise foul.

The spacing between the Hall effect device 18 and the magnet 24 is preferably in the range 0.5-2.5 mm, and preferably is of the order of 1 mm. While FIG. 5 is not drawn exactly to scale, it nevertheless indicates approximate proportions and dimensions for the other components of a sensor in which the magnet-to-Hall effect device spacing is about 1 mm.

The output cable 29 is connected to the circuitry described above with reference to FIGS. 1-3.

For the detection of non-respiratory movements, the device differs from that of FIGS. 4 and 5, since the magnet 24 is separated from the Hall effect device 18. The magnet can be mounted in a plastic retaining member similar to that 13 of FIG. 5, the plastic member being secured to a part of a patient where movement is to be detected (e.g. a patient's eyelid). The housing containing Hall device 18 is then mounted over the magnet 24 at a distance in the millimeter range therefrom.

Figure 6:
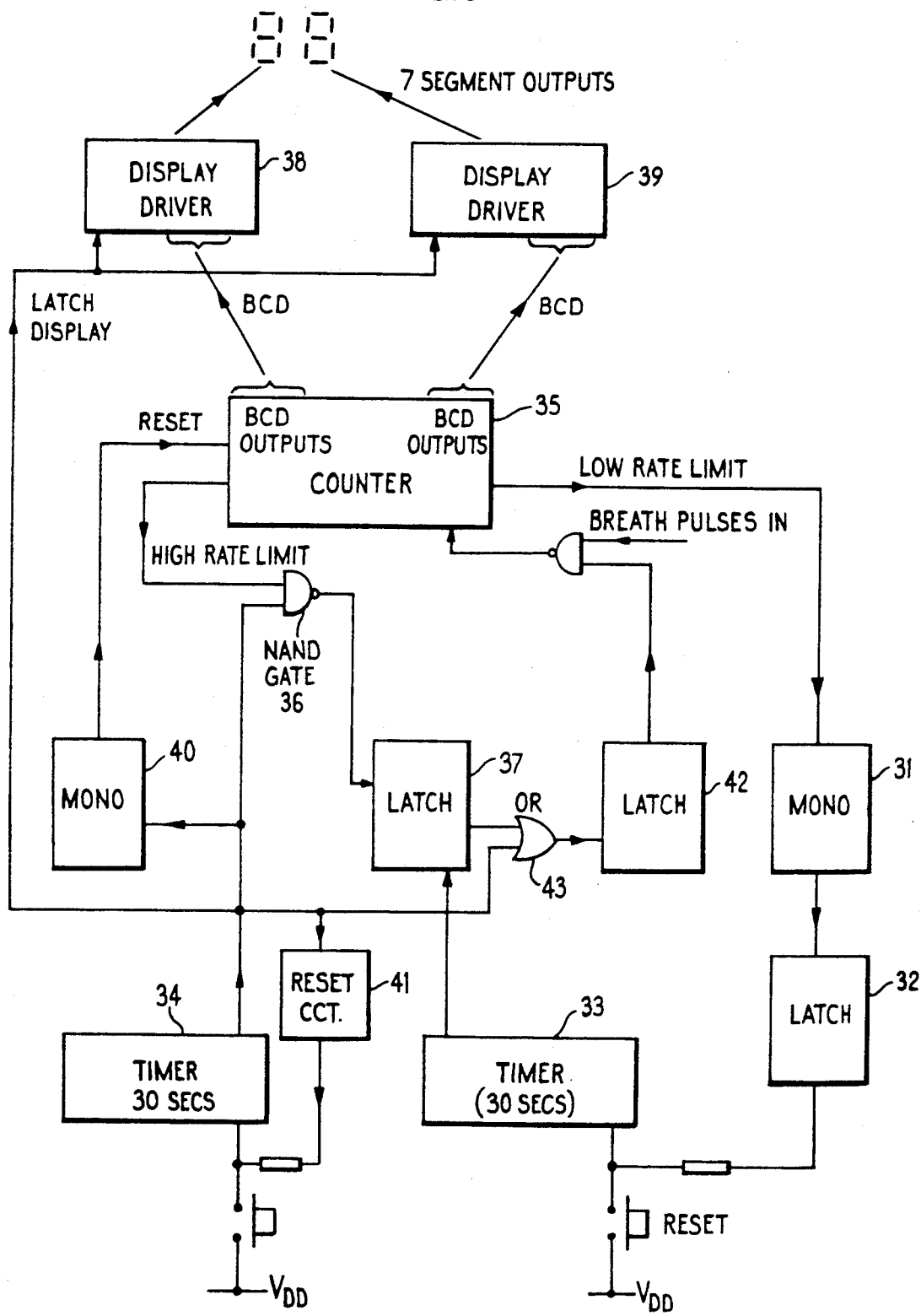
FIG. 6 shows a block circuit diagram of a breathing rate count/display circuit of this invention.

Referring next to FIG. 6, a circuit is shown which serves to count and display the breathing rate of a patient. In normal operation, the circuit has two rate limits arranged such that:

Low Rate < Breathing Rate < High Rate Limit

When the low rate count has been exceeded (in less than 30 seconds), a first monostable 31 is triggered which sets a first latch 32. Latch 32 being set prevents a first timer 33 from timing out, so that the timer 33 output is held high and a second alarm latch 37 is held reset.

Also for normal operation the high rate count will not be exceeded so that a second timer 34 times out before the "high rate limit" in counter 35 goes high. This ensures that the output of a NAND gate 36 stays high and again the alarm latch 37 is not set.

Timer 34 times out after 30 seconds. In timing out, it:
1. Latches the current count into display drivers 38 and 39;
2. Triggers a second monostable 40 which resets the counter 35 to zero; and
3. Reset itself via reset circuitry 41.

The whole process then repeats.

Low Rate Alarm Condition

In this case the low rate count is not exceeded within the 30-second time period.

Timer 33 and timer 34 both time out together.

When timer 33 times out it:
1. Sets latch 37 which raises the alarm; and
2. Latch 37 in turn sets a third latch 42 which stops the breath pulses being fed to the counter.

When timer 34 times out it:
1. Latches the current count into the display drivers 38 and 39.

This count will then be held displayed until the alarm has been accepted and the reset button pushed.

High Rate Alarm Condition

In this case timer 33 is reset early in the 30 second period, and this has the same effects as described above in relation to normal breathing operation. However, the "high rate output" from the counter 35 goes high before timer 34 times out. This makes the output of NAND gate 36 go low which sets latch 37 and raises the alarm. However, the counter 35 is allowed to continue to count till the end of the 30-second period so that the true high breathing rate will be latched into the display.

Timer 34 output will remain high to the end of the 30-second period. This prevents latch 42 from being set (via OR gate 43) so that the counter 35 continues to count. At the end of the 30-second period the count will be latched into the display, and the counter stopped.

Heart monitoring in accordance with this invention will now be described with reference to a preferred embodiment as exemplified in FIGS. 7-12.

Figure 7:
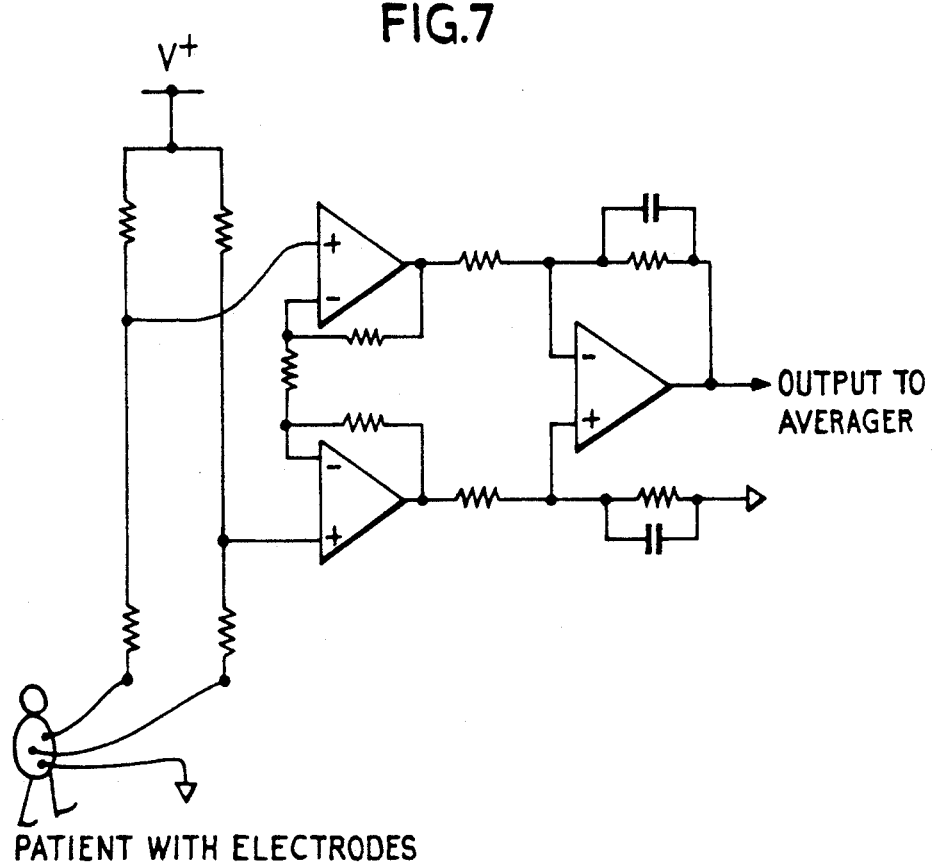
FIG. 7 shows the basic first stage amplification drawing used in a heart monitor.
Figure 8:
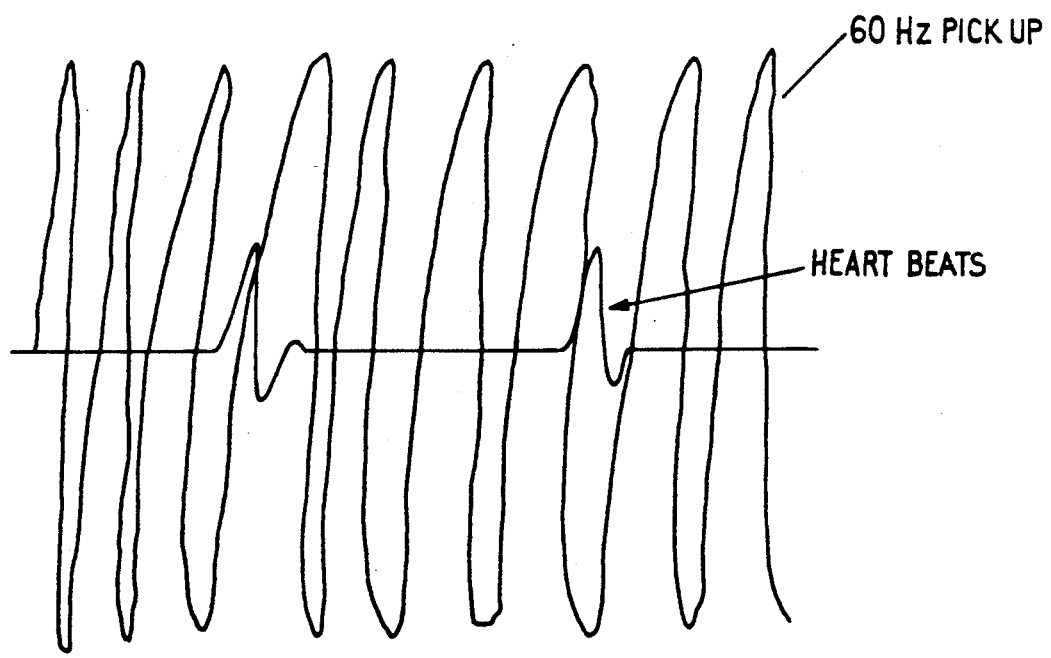
FIG. 8 shows a typical signal from the output of the amplification circuiting of FIG. 7.

Referring first to FIG. 7, the first stage amplifier is a triple op-amp instrumentation amplifier (this being a common and well-established technique). This arrangement ensures that any 60 Hz (or 50 Hz in England) signal which is picked up as a common mode signal by the body electrodes is reduced.

It is usual to follow this first stage amplifier by a notch rejection filter to further reduce the 60 Hz (50 Hz) pick-up, before further amplification of the heart rate signal takes place. Notch filters are difficult to design requiring tight tolerance components and fine tuning during manufacture.

An alternative method is presented in accordance with this invention which method requires no tuning and no specially selected components.

The signal leaving the first stage amplifier (see FIG. 8) comprises the heart beat signal buried in 60 Hz or 50 Hz pick-up signal which may be several magnitudes larger than the desired signal. The signal passes through an averager (described below with reference to FIG. 9) which has as its output a dc signal the magnitude of which depends directly on the magnitude of the 60 Hz or 50 Hz pick-up signal.

The heart beat signal then appears as a disturbance to this d.c. level so that in effect the roles of the signals have been reversed.

The detection of the heart beat signals (for counting purposes) is then accomplished by the detection circuitry as described hereinabove with reference to FIGS. 1-3 and 6.

Figure 9:
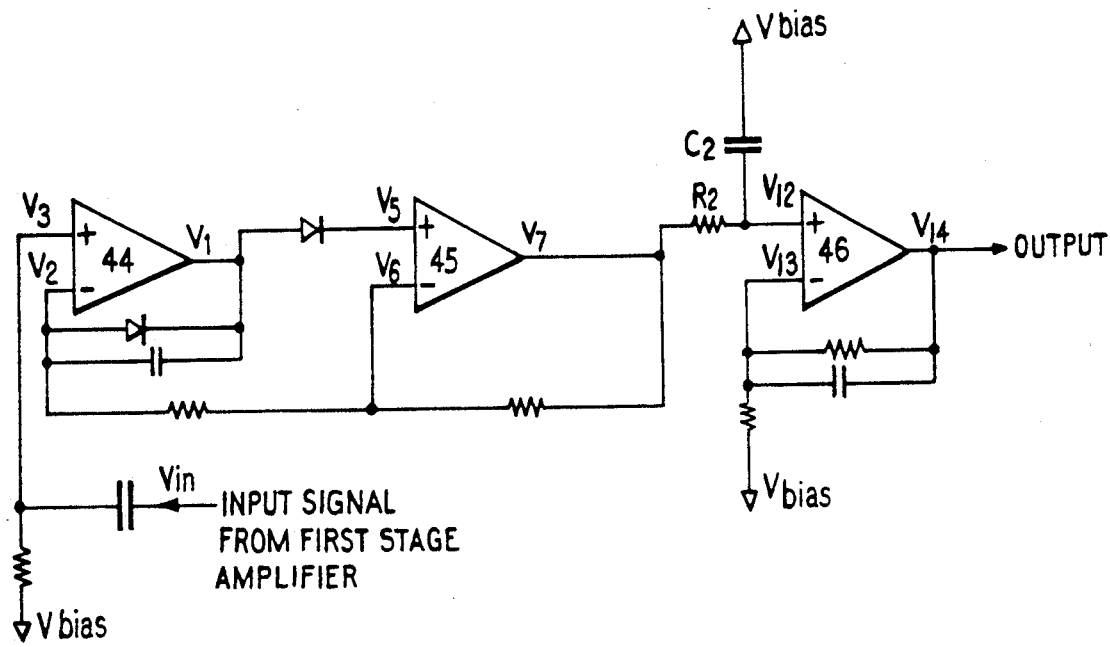
FIG. 9 shows in block form an average circuit of this invention.
Figure 10:
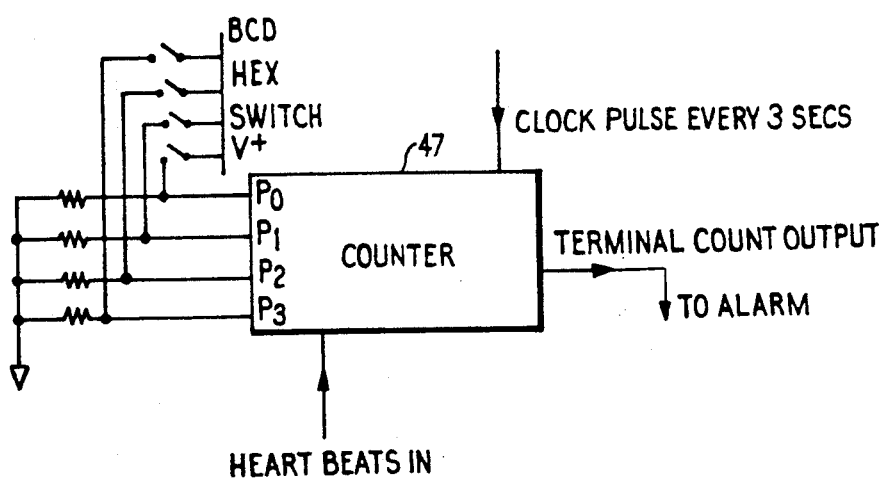
FIG. 10 shows part of a circuit for generating a high heart rate alarm.
Figure 11:
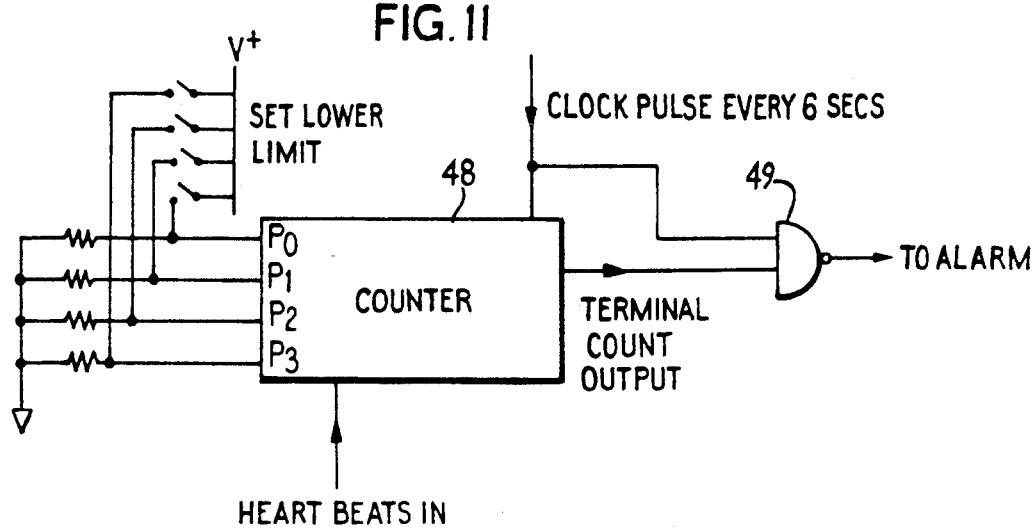
FIG. 11 shows part of a circuit for generating a high heart rate alarm.

Referring next to FIG. 9, an averager circuit is shown the purpose of which is to replace the conventional notch filter in a heart rate monitor.

Amplifiers 44 and 45 form a full wave rectifier, such that the voltage $V_7$ at the output of amplifier 45 is a full wave rectified version of $V_{in}$. This output voltage $V_7$ is smoothed by the resistor capacitor combination R2C2, and then further amplified by amplifier 46. The output voltage $V_{14}$ is applied as the input into another identical stage, i.e. it becomes $V_{in}$ into a second averager, then the output of this second averager will have a ripple frequency of 200 Hz or 240 Hz. It is thus preferred to employ two circuits as shown in FIG. 9, these connected in series. Further circuits can be added if desired so as to give even better discrimination.

This progressive doubling of the frequency of the interfering signal makes the filtering of the heart beat signal from the interfering pick-up progressively easier to achieve.

No tuning is required and no special selection of components is necessary.

The final output signal is then a dc voltage, the magnitude of which varies directly with the magnitude of the interfering pick-up. Superimposed upon this dc voltage is the heart beat signal. The detection of the heart beat signal is then achieved by pulse detection circuitry which is as shown in, and as, described above with reference to, FIG. 2.

Preferably, medical apparatus in accordance with this invention incorporates at least one heart rate condition alarm. Three such alarm circuits will now be described with reference to FIGS. 10-12. These circuits provide the facility to alarm in the event of:

1. The heart rate exceeding a pre-determined upper limit;
2. The heart rate falling below a pre-determined lower limit;
3. The heart rate suffering a 20% (approximately) reduction over a 30-second period.

High Heart Rate Detection

The high rate limit is set by the operator (doctor or nurse) by means of a 15 position switch on the unit. This switch is a hexadecimal switch which has a BCD output (Binary Coded Decimal) so that any number between 1 and 15 may be generated by the switch. The maximum heart rate that this embodiment of the unit will register is pre-selected to be 300 beats/minute. 300 beats/minute = 5 beats/second; counted over a 3-second period, the count would be 15. (This corresponds to the maximum number which can be set on the BCD HEX switch).

| Count over a 3-second period | × | Scale factor | = | Rate beats/min. |
|---|---|---|---|---|
| 15 | × | 20 | = | 300 |
| 14 | × | 20 | = | 280 |
| 13 | × | 20 | = | 260 |
| . | | . | | . |
| . | | . | | . |
| 5 | × | 20 | = | 100 |

The value of the high alarm rate is selected by the clinician and is set via the BCD Hex switch—e.g. 300(15), 280(14), etc. Every 3 seconds a clock pulse loads this number into counter 47. The counter 47 then subtracts each heartbeat in turn from this preset number. If within the period of 3 seconds the number of heart beats exceeds or is equal to the number set on the BCD switch, then the terminal count output is set and the alarm is triggered.

If the number of heart beats does not exceed the number set on the BCD switch within the 3-second period, then the terminal count output will not be triggered, the number set at the P0 to P3 inputs will be loaded once more and the process repeats.

Low Heart Rate Detection

A range of lower limits is needed according to the age of the patient. Thus for a maximum lower limit of 150 beats/minute = 150/60 beats/second, then over a 6-second period, the count = $150/60 \times 6 = 15$.

Hence, as described above for the high rate alarm,

| Count over a 6-second period | × | Scale factor | = | Rate beats/min. |
|---|---|---|---|---|
| 15 | × | 10 | = | 150 |
| 14 | × | 10 | = | 140 |
| . | | . | | . |
| . | | . | | . |
| 3 | × | 10 | = | 30 |

The lower limit is selectable between 30 and 150 beats/minute in increments of 10. In this case, if the number of heart beats which occurs in 6 seconds DOES NOT exceed that number set on the switch, we need to alarm.

The terminal count output from counter 48 (FIG. 11) is normally high; it goes low when the terminal count is reached. If the terminal count output is still high when the clock pulse arrives, the output of NAND gate 49 goes low and sets the alarm. If the terminal count output is low when the clock pulse arrives (i.e. the heart rate is above the lower limit setting) then as with the high rate counter, the number set on the switches is loaded into the counter once more and the process repeats.

Decelerating Heart Rate

To detect a 20% deceleration over a 30-second period, the monitor is arranged to:
1. Establish the heart rate (averaged over a 4-second period);
2. Wait 30 seconds;
3. Establish a new heart rate and compare with that in 1. If it has dropped by 20%, alarm.

As an example, consider the case in which the initial count over 4 seconds is 12, i.e. 3 pulses/second, vis-a-vis the following time-count conditions: If at the end of 30 seconds the rate has dropped by 20% i.e. the rate will now be 2.4 pulses/second, and if we now count at this rate for 5 seconds, the count would be $2.4 \times 5 = 12$, i.e. the same as what we started with. If the rate had not dropped, then the count at the end of 5 seconds would be $3 \times 5 = 15$, i.e. the count would be greater than our initial count.

Therefore for a 20% reduction or more, we alarm if the count taken over a 5-second span is less than or equal to the count taken over a 4-second span (but measured 30 seconds earlier).

Figure 12:
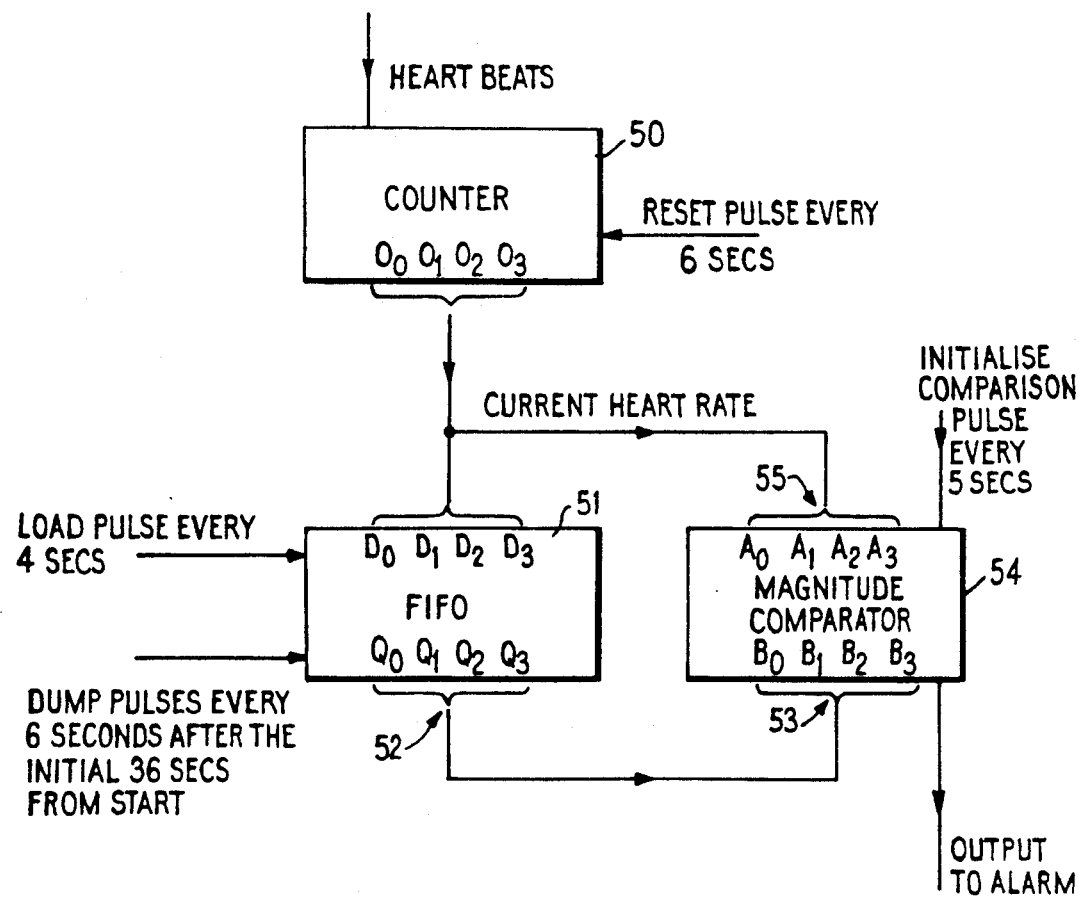
FIG. 12 shows a circuit for detecting a decelerating heart rate.

The circuiting adopted in one embodiment to measure deceleration of heart rate will now be described with reference to FIG. 12.

Heart beats are counted in a 6-second time slot by counter 50, i.e. after 6 seconds the counter is reset to zero and the count re-started. The counter contents are continuously available (in binary form) at the outputs $O_0$, $O_1$, $O_2$, $O_3$.

After 4 seconds (from the start of a 6-second slot) the count current in the counter 50 is loaded into the FIFO register 51, (First In First Out), where it is held for 30 seconds before being made available at the FIFO output port 52 and presented to the "B" inputs 53 of a magnitude comparator 54. Subsequent 4-second counts are loaded into the FIFO 51 for each 6-second time slot where they in turn are held for 30 seconds before being dumped out.

The magnitude comparator 54 compares the magnitude of two binary numbers presented at its "A" and "B" inputs. The comparison is made 5 seconds after the start of a 6-second time slot by an "initialize comparison" pulse. The magnitude comparator 54 has the current counter contents applied to its "A" input terminals at 55. After 5 seconds into a cycle, the "initialize comparison" pulse arrives so that the current count taken over 5 seconds is compared with the count taken over 4 seconds (30 seconds earlier). An output pulse (alarm trigger) is generated from the comparator 54 if the magnitude of the binary number at the A terminals is less than or equal to the number at the B terminals.

Medical apparatus in accordance with this invention may incorporate one or both of the respiration monitor and heart rate monitor described above.

What is claimed is:

1. A displacement sensor for sensing the movement of a surface of a patient comprising: (a) a housing (1) formed at least in part of resilient material that defines a contact portion (13) that is configured and constructed to rest, when in use, in contact with the surface the movement of which is to be sensed; (6) a displacement transducer (28) including a Hall effect device (18) mounted in a normally spaced position adjacent said contact portion (13); (c) a magnetic activator (24) for said displacement transducer (28,18) mounted for movement with the constant portion (13) such that, when in use the surface the movement of which is to be detected does not move, the contact portion (13) moves, thus changing the spacing between the activator (24) and the Hall effect device thereby causing the Hall effect device to produce an output voltage; (d) a level detector means which receives the output of the Hall effect device and produces an output which varies therewith; (e) means for applying a dynamic reference voltage to the input of the level detector which varies with the output of the Hall effect device; (f) alarm means connected to respond to the output of the level detector for indicating movement of said surface.

2. The displacement sensor of claim 1 wherein the housing defines cavity having a wall portion, the contact portion being in the form of a cap, the housing being formed substantially of silicone rubber.

3. The displacement sensor of claim 2 further comprising a retaining strap for attaching the sensor to the surface whose movement is to be sensed.

4. The displacement sensor of claim 3, wherein the housing comprises an annular wall portion secured to and extending away from the cap, the cap and annular walls defining the cavity, the cap being thicker than in the annular walls, and wherein the cap comprises means forming a recess debouching into said internal cavity, and wherein said activator is mounted within said recess and wherein the displacement transducer forms a wall portion of the cavity.

5. The displacement sensor of claim 3 wherein said cavity is defined by the cap and by a downwardly and outwardly extending frustoconical side wall portion adjoining the cap portion, and by a relatively thinner walled portion adjoining said side wall portion.

6. The displacement sensor of claim 5, wherein the cap has formed thereupon an annular ring which surrounds said recess and which projects into the cavity.

7. The displacement sensor of claim 6, wherein said signal output means comprises a printed circuit board that forms a portion of the wall of the cavity and to which the Hall effect device is connected.

8. A displacement sensor comprising a housing formed of a resilient material defining a generally planar cap, a frustoconical side wall portion joined to the cap and extending away from the plane of the cap and outwardly therefrom, and a second wall portion adjoining said side wall portion, the side wall and second wall being thinner than the cap; (b) a Hall effect device mounted in proximity to but spaced from the cap; (c) a permanent magnet supported by the cap spaced apart from said Hall effect device and being movable relative thereto in response to movement of the cap; (d) a level detector means which receives the output of the Hall effect device and produces an output which varies therewith; (e) means for applying a dynamic reference voltage to the input of the level detector which varies with the output of the Hall effect device; (f) alarm means connected to respond to the output of the level detector for indicating movement of said surface.

9. A displacement sensor for sensing the movement of a surface comprising: (a) a housing (1) comprising a cap (13) which is configured and constructed to rest, when in use, in contact with the surface whose movement is to be sensed; (b) a displacement transducer (28) including a Hall effect device (18) mounted so as to be spaced from said cap (13); (c) a magnetic activator (24) for said displacement transducer (28, 18) mounted for movement with the cap (13) such that movement of the cap (13) changes the distance between the activator and the transducer thus producing a change in the output voltage of the Hall effect device; (d) a level detector means which receives the output of the Mall effect device and produces an output which varies therewith; (e) means for applying a dynamic reference voltage to the input of the level detector which varies with the output of the Hall effect device; (f) alarm means connected to respond to the output of the level detector for indicating movement of said surface.

* * * * *